United States Patent
Fisker et al.

(10) Patent No.: US 10,561,479 B2
(45) Date of Patent: Feb. 18, 2020

(54) FACEBOW AND METHOD OF USING A FACEBOW

(71) Applicants: 3Shape A/S, Copenhagen K (DK); SAM Präzisionstechnik GmbH, Gauting (DE)

(72) Inventors: Rune Fisker, Virum (DK); Florian Arne Mack, Munich (DE); Lars Henriksen, Bagsvaerd (DK)

(73) Assignees: 3Shape A/S, Copenhagen K (DK); Sam Prazisionstechnik GmbH, Gauting (DE)

( * ) Notice: Subject to any disclaimer, the term of this patent is extended or adjusted under 35 U.S.C. 154(b) by 23 days.

(21) Appl. No.: 15/508,716

(22) PCT Filed: Sep. 3, 2015

(86) PCT No.: PCT/EP2015/070148
§ 371 (c)(1),
(2) Date: Mar. 3, 2017

(87) PCT Pub. No.: WO2016/034672
PCT Pub. Date: Mar. 10, 2016

(65) Prior Publication Data
US 2017/0273762 A1  Sep. 28, 2017

(30) Foreign Application Priority Data
Sep. 4, 2014  (DK) .................................. 2014 70540

(51) Int. Cl.
*A61C 11/00* (2006.01)
*A61C 19/045* (2006.01)
(52) U.S. Cl.
CPC .......... *A61C 11/005* (2013.01); *A61C 19/045* (2013.01)

(58) Field of Classification Search
CPC ..... A61C 11/00; A61C 11/005; A61C 19/045; A61C 13/0004; A61C 6/14; A61C 6/5247; A61B 5/4542
See application file for complete search history.

(56) References Cited

U.S. PATENT DOCUMENTS

| | | | | | |
|---|---|---|---|---|---|
| 4,616,998 | A | * | 10/1986 | Wong .................. | A61C 19/045 33/514 |
| 4,892,480 | A | * | 1/1990 | Levandoski ......... | A61C 19/045 433/73 |

(Continued)

FOREIGN PATENT DOCUMENTS

| | | |
|---|---|---|
| DE | 10 2009 044 147 A1 | 4/2011 |
| JP | 60-86316 U | 6/1985 |

(Continued)

OTHER PUBLICATIONS

International Search Report (PCT/ISA/210) dated Oct. 30, 2015, by the European Patent Office as the International Searching Authority for International Application No. PCT/EP2015/070148.

(Continued)

*Primary Examiner* — Sang H Nguyen
(74) *Attorney, Agent, or Firm* — Buchanan Ingersoll & Rooney PC (57) ABSTRACT

Disclosed is a method for determining the geometrical relationship between a patient's dental structure and a reference feature on the head of the patient, the method including obtaining a first digital representation of a facebow including a fiducial marker, an adjustable pin member attached to the facebow and an attachment section of the facebow for placing the facebow in relation to the reference feature, the attachment section having a geometrical relationship with the fiducial marker; obtaining a second digital representation comprising a part of the patient's dental structure, a part of the pin member, and part of the facebow (Continued)

including the fiducial marker; obtaining information about the placement of the attachment section relative to the reference feature; and determining the geometrical relationship between the patient's dental structure and the reference feature based on the first and second digital representations and the placement of the attachment section.

13 Claims, 6 Drawing Sheets

(56) References Cited

U.S. PATENT DOCUMENTS

| | | | | |
|---|---|---|---|---|
| 5,090,901 | A * | 2/1992 | Levandoski | A61C 19/045 433/56 |
| 5,927,973 | A * | 7/1999 | Hanebaum | A61C 19/04 33/513 |
| 6,109,917 | A * | 8/2000 | Lee | A61C 19/045 433/68 |
| 6,152,731 | A * | 11/2000 | Jordan | A61C 13/0003 433/69 |
| 6,152,732 | A * | 11/2000 | Lindekugel | A61C 19/045 433/73 |
| 6,179,612 | B1 * | 1/2001 | Reusch | A61C 19/045 433/69 |
| 7,048,539 | B2 * | 5/2006 | Mack | A61C 19/045 433/73 |
| 8,287,276 | B2 * | 10/2012 | Klett | A61C 19/045 433/54 |
| 8,366,442 | B2 * | 2/2013 | Schmitt | A61C 13/0004 433/73 |
| 2004/0032594 | A1 * | 2/2004 | Weber | A61C 13/0004 356/601 |
| 2005/0186540 | A1 * | 8/2005 | Taub | A61C 13/0004 433/223 |
| 2009/0220927 | A1 * | 9/2009 | Amann | A61C 11/00 434/264 |
| 2010/0191510 | A1 * | 7/2010 | Kopelman | A61C 9/0066 703/1 |
| 2012/0179281 | A1 * | 7/2012 | Steingart | A61C 13/0004 700/97 |
| 2014/0067337 | A1 | 3/2014 | Kopelman | |
| 2014/0170583 | A1 * | 6/2014 | Kuo | A61B 1/24 433/3 |
| 2014/0170587 | A1 | 6/2014 | Kopelman | |
| 2014/0242539 | A1 * | 8/2014 | Fisker | A61C 13/0004 433/54 |
| 2016/0008107 | A1 * | 1/2016 | Brunner | A61C 9/0006 433/41 |
| 2018/0147039 | A1 * | 5/2018 | Carlson | A61B 5/00 |

FOREIGN PATENT DOCUMENTS

WO    WO 2011/073436 A1    6/2011
WO    WO 2011/103876 A1    9/2011

OTHER PUBLICATIONS

Written Opinion (PCT/ISA/237) dated Oct. 30, 2015, by the European Patent Office as the International Searching Authority for International Application No. PCT/EP2015/070148.

* cited by examiner

100

```
┌─────────────────────────────────────┐
│ A digital representation of a facebow is │  101
│ received on a computer.             │
└─────────────────────────────────────┘
                  │
                  ▼
┌─────────────────────────────────────┐
│ A digital representation comprising a part of │
│ the patient's dental structure, a part of a pin │  102
│ member and a part of a facebow is   │
│ received on a computer.             │
└─────────────────────────────────────┘
                  │
                  ▼
┌─────────────────────────────────────┐
│ The geometrical relationship between the │
│ patient's dental structure and a reference │  103
│ feature on the patient is calculated. │
└─────────────────────────────────────┘
```

201 — Receiving a digital representation of a facebow on a computer, from a library of digital representations of facebows.

202 — Scanning the patient's upper and lower jaws to create a digital 3D representation of each of the upper and lower jaws

203 — Scanning the patient's upper and lower jaws in occlusion to create a digital 3D representation patient's jaws in occlusion

204 — Attaching a facebow to the patient, the facebow having a pin member and the facebow having a geometrical relationship with a reference feature of the patient

205 — Scanning a part of the patients upper jaw along with at least part of the pin member and at least a part of the facebow, to create a digital representation of upper jaw and the part of the facebow

206 — Defining a a co-ordinate system and aligning the digital representation of step 204 and the digital representation from step 201 in the co-ordinate system

207 — Calculating the geometrical relationship between the patient's dental structure and the reference feature

208 — Using the geometrical relationship found in step 207 to insert the digital representations of the patient's upper and lower jaw into a virtual articulator

FACEBOW AND METHOD OF USING A FACEBOW

FIELD OF THE INVENTION

This invention generally relates to digital dentistry and virtual articulators. More particularly, the invention relates to a method for determining the correct anatomical relationship between a patient's dentition and a reference feature on the patient, and the use of this relationship for transferring a digital representation of the patient's dentition into a virtual articulator.

BACKGROUND OF THE INVENTION

An articulator is a mechanical device which provides a simplified geometrical model of the cranium for simulating the relative movements of the human jaws for testing occlusion of teeth. An articulator is used by a dental technician when modeling dental restorations for a patient, and the dental technician may alternate between modeling the restorations and evaluating the function of the bite or occlusion using the articulator. For testing collision of teeth in the upper and lower jaw, the dental technician can use carbon copy paper placed between the teeth of the two jaws in the articulator, and the colliding teeth will be thus colored, when the jaws are moved.

A facebow is a mechanical device which is used to register the relationship of the patient's maxillary arch in three planes of space and transfer this information into an articulator that can be adjusted to simulate the patient's jaw movements. The relationship is two-fold: to establish the functional relationship of the maxillary arch to the axis of rotation for proper function and to analyze the esthetic relationship of the maxillary arch to the patient's face for optimal esthetics.

Virtual articulators are digital representations of articulators and are well known in the art, for example from WO2011/103876 registered to the current applicant.

US2014/0067337 describes a method and system for providing patient data useful for dental procedures, including scanning a dental structure of a patient when coupled to a geometric structure to provide a virtual model representative of the coupling and the dental structure, and relating the virtual model to a body reference of the patient.

Previously, it has been necessary to take physical impressions of a patient's upper and lower jaws, and scan these physical impressions in order to obtain a digital dental model of a patient, which can be inserted into the virtual articulator.

It remains a problem to determine the relationship between a patient's upper and lower jaw and the hinge axis of the jaws, without the need for making physical models of the patient's dental structure.

It remains a problem to transfer a digital representation of the patients dental structure into a virtual articulator without the need for making physical models of the patient's dental structure.

SUMMARY

Disclosed is a method for determining the geometrical relationship between at least a first part of a patient's dental structure and at least one reference feature on the head of the patient, the method comprising:
obtaining a first digital representation of a facebow including a fiducial marker, an adjustable pin member attached to the facebow and an attachment section of the facebow for placing the facebow in relation to the reference feature, the attachment section having a geometrical relationship with the fiducial marker;
obtaining a second digital representation comprising a part of the patient's dental structure, at least a part of the pin member, and at least a part of the facebow including the fiducial marker;
obtaining information about the placement of the attachment section relative to the reference feature; and
determining the geometrical relationship between the part of the patient's dental structure and the reference feature based on the first and second digital representations and the information about the placement of the attachment section.

All facebows are designed to be attached to a patient in a specific way. For example, a facebow may have condylar rods or ear pieces, for attaching the facebow to the patient's condyles or ear canals respectively. Therefore, the information about which reference feature on the head of the patient the facebow was attached to, may be known immediately from knowing which facebow was used. It could also be that the dentist decided to place the facebow in a slightly different manner than normally intended, and this information could then be written down or noted in the file containing the digital representations by the dentist.

Therefore, since there is a digital representation of the facebow, it is only necessary to obtain a second digital representation comprising a part of the patient's dental structure, a part of the pin member and a part of the facebow including the fiducial marker to determine the geometrical relationship between the patient's dental structure and the reference feature.

Consequently, it is an advantage that the geometrical relationship between the patient's dental structure and the reference feature can be determined without the need for making physical models of the patient's dental structure. Rather, all the steps of the method can be performed digitally.

Another advantage of this embodiment is that when the facebow comprises a pin member, there is no need for using a bite fork, and there is no need for using impression material, therefore it is more comfortable for the patient and the facebow has a simpler construction. Also, it is easier to scan part(s) of the patient's dental structure along with the pin member using an intraoral scanner. It would be difficult to scan the patient's dental structure along with a bite plate using an intraoral scanner.

In some embodiments, the method further comprises obtaining information about which specific reference feature, on the head of the patient, the facebow was attached to.

In some embodiments, the method further comprises determining the geometrical relationship between the patient's dental structure and the reference feature by:
defining a co-ordinate system;
inserting and aligning the first and second digital representations in the co-ordinate system so that common features overlap;
calculating the geometrical relationship between the patient's dental structure and the reference feature based on the known relationship between the overlapping features and the reference feature.

Aligning the first and second digital representations may for example be done by computing transformation matrices that define the relationship between each of the digital representations and the co-ordinate system.

In some embodiments, the method further comprises:

obtaining a third digital representation comprising the patient's upper jaw;

aligning the second and third digital representations in a common co-ordinate system; and coupling the information about the geometrical relationship to the third digital representation.

An advantage of these embodiments is that there is obtained a digital representation of the full upper or lower jaw of the patient where the relationship to the reference feature is known, but without having the digital representation of the facebow to obstruct the view.

In some embodiments, the method further comprises:

obtaining a fourth digital representation comprising the lower jaw of the patient.

In some embodiments, the method further comprises:

obtaining a fifth digital representation comprising at least part of the upper and lower jaws in occlusion.

An advantage of these embodiments is that having a digital representation of the full upper and lower jaw, makes it suitable to transfer the digital representations into a virtual articulator, in a parallel workflow to that which is done in the traditional method where physical models of the upper and lower jaw are inserted into a physical articulator.

In some embodiments, the method further comprises:

Transferring one or more of the third, fourth or fifth digital representations into a virtual articulator based on the geometrical relationship between the patient's dental structure and the at least one reference feature.

In some embodiments, the method further comprises obtaining the digital representations by scanning using an intraoral scanner.

In some embodiments, the reference feature comprises one or more of the ear canal, the temporomandibular joint, the nasion, the ala of the nose, and/or the orbitale.

The reference feature(s) can in principle be any feature on the patient, both in the form of features belonging to the anatomy of the patient as well as for example radiopaque markers placed on the patient's face, as long as it is possible, with the aid of the reference feature, to determine how at least one of the digital representations can be inserted into the virtual articulator.

In some embodiments, the reference feature(s) is used to determine one of the Frankfort plane, the Camper plane, the Denar plane, the maxilla plane, the mandible plane and/or the occlusal plane, and this plane is used in transferring the digital representation into the virtual articulator.

Once one of these planes has been determined, the insertion of the digital representations into the virtual articulator can be performed as explained in WO2011/103876.

Normally, a facebow is made to correspond with a matching articulator. This means that once the facebow has been secured to the patient's head and the patient has bit down on a bitefork, the plane that is relevant for that particular articulator will be known. Then the bitefork including impression material will be sent to a laboratory to make a physical model which can be inserted into the physical articulator.

For example, a facebow may be configured to be inserted in the ear-canals of the patient, and have an orbital pointer for determining the position of the nasion. The three points consisting of the two ear canals and the nasion will then define a plane in 3D space, which can be used to insert the physical models into a articulator.

Likewise in the current invention, once the necessary scans have been obtained, the facebow used will provide the geometry needed to define the plane that is relevant for the particular virtual articulator being used.

In some embodiments, the method further comprises making at least one of the digital representations of the upper and lower jaws into a physical model and placing the physical model in a physical articulator.

An advantage of these embodiments is that the dentist or dental technician may be more comfortable working with physical models and physical articulators, yet the physical models have been made without having to subject the patient to taking physical impressions of his/her upper and/or lower jaws.

Particularly disclosed is a facebow, comprising:

A U-shaped frame;

An attachment section comprising two ear-pieces or condylar rods;

A locking device;

A third reference point; and a pin member configured to touch the patient's teeth without the need for the patient to bite down on it.

An advantage of this aspect is that unlike all current facebows, the facebow according to this invention does not include a biteplate. This makes it more comfortable for the patient, no impression material needs to be used, and the facebow has a simpler construction. Also, it makes it easier to scan part(s) of the patient's dental structure along with the pin member. The pin member may be movably attached to the facebow, so that it can be adjusted according to the exact geometry of each individual patient's face.

In some embodiments the pin member comprises markings visible in the field of view of a scanner.

The markings can be in any form, for example geometric shapes such as circles, squares, triangle, lines or any other shape or a random or pseudo-random pattern, or they could be colour markings. The markings can for example be etched into the pin so as to have a 3D effect when scanned, and this would make it easier to distinguish the markings in the digital representation.

An advantage of these embodiments, is that it makes it possible to make the pin member out of any material, even material which is not usually easy to scan with an intraoral scanner, for example materials with a high reflectivity.

Another advantage of these embodiments, is that it makes it easier to stitch together the independent subscans into a single digital representation comprising the pin member, since for example the pin member could made out of a material where it is not easy to differentiate the different parts of the pin member, or the pin can be bigger than the field of view of the scanner, which will make it difficult to stitch together the different subscans without any distinguishing markings that can be used to determine which part of the pin member has been scanned.

In some embodiments the pin member comprises a groove configured so a part of the patient's teeth fit into the groove.

An advantage of these embodiments is that the pin member rests more securely on the patient's teeth, and it is less likely to accidentally knock the pin member out of alignment during scanning.

In some embodiments the facebow comprises at least one scannable fiducial marker.

The fiducial marker can be in any form, for example geometric shapes such as circles, squares, triangle, lines, spheres or any other shape or a random or pseudo-random pattern, or they can be colour markings. The markings can for example be etched into the pin so as to have a 3D effect when scanned, and this will make it easier to distinguish the markers in the digital representation.

In some embodiments the fiducial marker on the facebow may be in the form of an indentation such as a semi-sphere.

This will make it easier to achieve a very accurate determination of the actual position of the facebow in the scan.

An advantage of these embodiments is that it makes it easier to identify a part of the facebow which is static with regard to the reference feature on the patient, so it is easier to know when enough of the facebow has been scanned in order to have a good correlation between the digital representations of the patient's dental structure and the reference feature.

It should be noted that in the above methods, the steps are interchangeable. For example, the second, third, fourth and/or fifth digital representation may be obtained before the first digital representation.

The term "digital representation" is used in this application as synonymous with "numerical model", 3D model, computer generated model, virtual model and other such terms, and relates to a representation in a computer environment of a physical object, for example a patient's dental structure or a part thereof, or of a physical model of a patient's dental structure or a part thereof, for example. A digital representation may for example be a visual depiction, a mathematical formulation or a set of stored data.

For example, when a jaw is scanned using an intra-oral scanner such as the TRIOS scanner by 3Shape, a point cloud will be generated. Each point is defined by its position in space. This is considered a 3D digital representation of the jaw, however, a data file containing all the data concerning the point cloud is very large and often contains redundant information. Thus, in order to facilitate handling of the data it can be transformed into data describing a polygon mesh representing the jaw. The polygon mesh data is easier to handle but still provides a 3D representation of the jaw. Finally, the polygon mesh data may be used to visually depict the jaw. This visual depiction of the jaw on a computer monitor or printed on a piece of paper is also considered a 3D digital representation.

Accordingly it can be understood that the term "digital representation" covers anything that as its core function serves to represent anything in the physical space that may be observed, detected or otherwise recorded.

The term "scanning" may refer to any method for obtaining 3D topographic surface data, including both contact and non-contact methods, for example stereoscopic, laser triangulation, off-axis aperture imaging, confocal imaging, chromatic confocal imaging, conoscopic holography or deconvolution imaging.

The term "obtaining" may refer to physically acquiring for example a scan of a patient's dental structure, but it may also refer for example to loading into a computer a digital representation previously acquired.

The term "facebow" refers to any structure used to record the positional relations of the maxillary or mandibular arch to the temporomandibular joints and which can help orient dental casts in this same relationship to the opening axis of an articulator.

The term "dental structure" may refer to any of the patient's dentition or any part thereof, including a tooth or teeth or a part of a tooth or teeth, the oral cavity or parts thereof, a preparation or prostheses or parts thereof, or the maxillary or mandibular arch or both or parts thereof, or any other structure associated with a patient's dental anatomy.

The term "pin member" refers to a part of the facebow which contacts the patient's teeth. It is different from a biteplate, in that the patient does not need to bite down on the pin member in order to achieve a locked position between the dental structure and the facebow.

The term "hinge axis" refers to a line that passes through the left and right mandibular condyles and coincides with the center of rotation of the mandible.

The term "fiducial" refers to a feature or object used in the field of view the imaging system which appears in the image/scan produced, for use as a point of reference.

BRIEF DESCRIPTION OF THE DRAWINGS

The above and/or additional objects, features and advantages of the present invention, will be further elucidated by the following illustrative and non-limiting detailed description of embodiments of the present invention, with reference to the appended drawings, wherein.

DETAILED DESCRIPTION

In the following description, reference is made to the accompanying figures, which show by way of illustration how the invention may be practiced.

Figure 1:
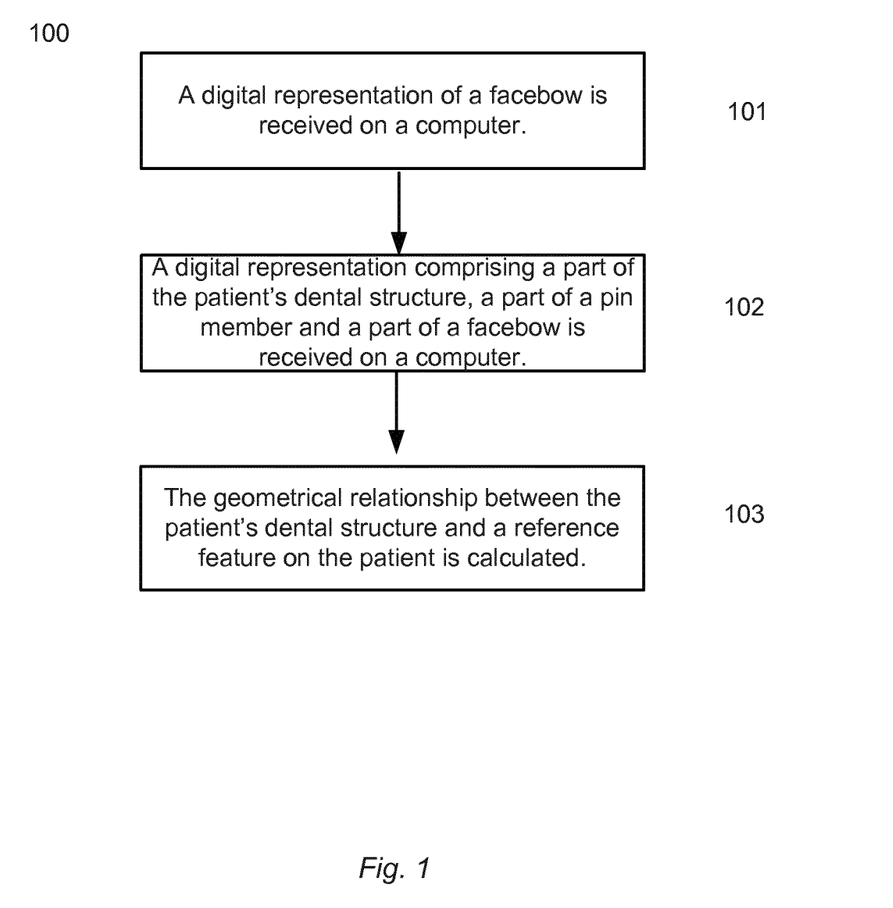
FIG. 1 shows a flow diagram of a method according to an embodiment of the invention.

FIG. 1 shows a flow chart of a workflow (100) according to an embodiment of the invention. In step (101), a first digital representation of a facebow is received on a computer. The first digital representation may be obtained for example from a library of digital representations of various facebows. The library can be on the computer or on a separate server, with the computer receiving the first digital representation over a network, for example the internet. The first digital representation comprises a fiducial marker, an adjustable pin member attached to the facebow and an attachment section of the facebow for placing the facebow in relation to the reference feature, the attachment section having a known geometrical relationship with the fiducial marker. In step (102), a second digital representation comprising a part of the patient's dental structure, at least a part of the pin member, and at least a part of the facebow including the fiducial marker is received on the computer. The second digital representation may have been taken previously, and stored on the computer or on a server. In step (103), a computer program then calculates the geometrical relationship between the patient's dental structure and the reference feature based on the first and second digital representations. The calculation can for example be done by defining a common co-ordinate system between the first and second digital representations. The two digital representations can then be represented by transformation matrices that define the relationship between each of the digital representations and the co-ordinate system. In this way, each point of the digital representations, will then have a co-ordinate in the common coordinate system. Since the second digital representation includes the fiducial marker of the facebow, and the fiducial marker has a known geometrical relationship with the reference feature, it is then possible to calculate the relationship between the patient's dental structure and the reference feature.

Figure 2:
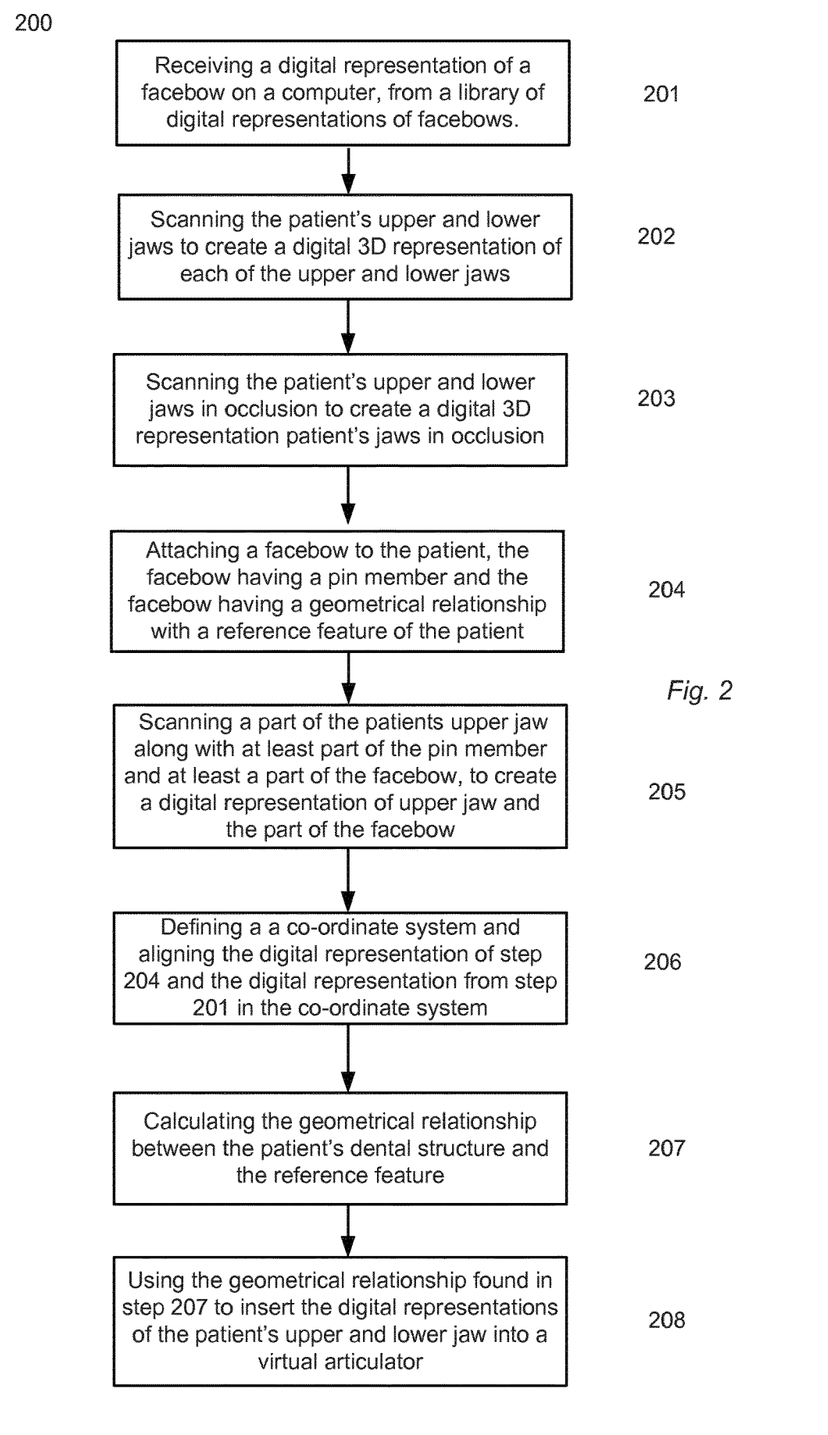
FIG. 2 shows a flow diagram of a method according to another embodiment of the invention.

FIG. 2 shows a flow chart of a workflow (200) according to an embodiment of the invention. In step (201), a digital representation of a facebow is loaded into a computer. The facebow can for example be selected from a library of facebows stored on the computer or on a server. In step (202), a digital representation of each of the patient's upper and lower jaws is taken using an intraoral scanner, for example the TRIOS scanner by 3Shape. In step (203) a digital representation of the patient's jaws in occlusion may also optionally be taken using the intraoral scanner. In step (204), a facebow with a pin member instead of a bite plate is fitted to the patient. This physical facebow should correspond to the digital representation loaded into the computer in step (201). The facebow has a geometrical relationship with a reference feature on the patient, for example the ear canal, the condyles or the temporomandibular joint. In step (205), a digital representation of part of the patient's dental structure, a part of the pin member, and a part of the facebow including a fiducial marker, is taken using the intraoral scanner. The pin member is configured to touch the patient's teeth without the patient needing to bite down on it, and replaces the biteplate or bitefork which is normally a part of facebows. The fiducial marker should be easily recognizable in the digital representation, to give the most accurate fit possible. All the digital representations are received on a computer. In step (206), a co-ordinate system is defined, and the digital representations from step (202) of the patient's upper jaw and the digital representation from step (205) are aligned using the defined co-ordinate system. This can be done, for example, by calculating transformation matrices that describe the relationship between each point in each digital representation, and the co-ordinate system. In step (207), the geometrical relationship between the patient's dental structure and the reference feature is calculated. Since the relationship between the fiducial marker and the reference feature is known, once the digital representations are aligned in step (206), it is possible to calculate the geometrical relationship between the patient's dental structure and the reference feature. In step (208) the digital representations of the patient's upper and lower jaw are inserted into a virtual articulator based on the geometrical relationship found in step (207). This can for example be done by defining a plane, using the relationship between the reference features on the patient that have been determined in step (207), and the third reference point known from the facebow. This plane corresponds to the plane used to place the representations of the patient's jaws in a virtual and/or physical articulator. For example, in step (207), the relationship between the patient's dental structure and the reference feature, for example the ear canals of the patient, is determined. The third point needed to define the plane may be for example the nasion, but could be any other reference feature defined by the facebow, and this information will be known because for each type of facebow, this reference point will always be the same. There may of course be a difference in geometry of each patient's face, but the difference in placement of the nasion relative to the ear canals may be negligible when it is only used to define the plane. Alternatively, information about the placement of the nasion could be entered into the digital representation of the facebow, the person performing the scan could measure it, or a separate scan of the part of the facebow attached to the nasion could be performed. This digital representation could then be aligned with the other digital representations in the common co-ordinate system. Then the geometrical relationship between the patient's dental structure and the nasion could be calculated the same way as in step (207).

Figure 3:
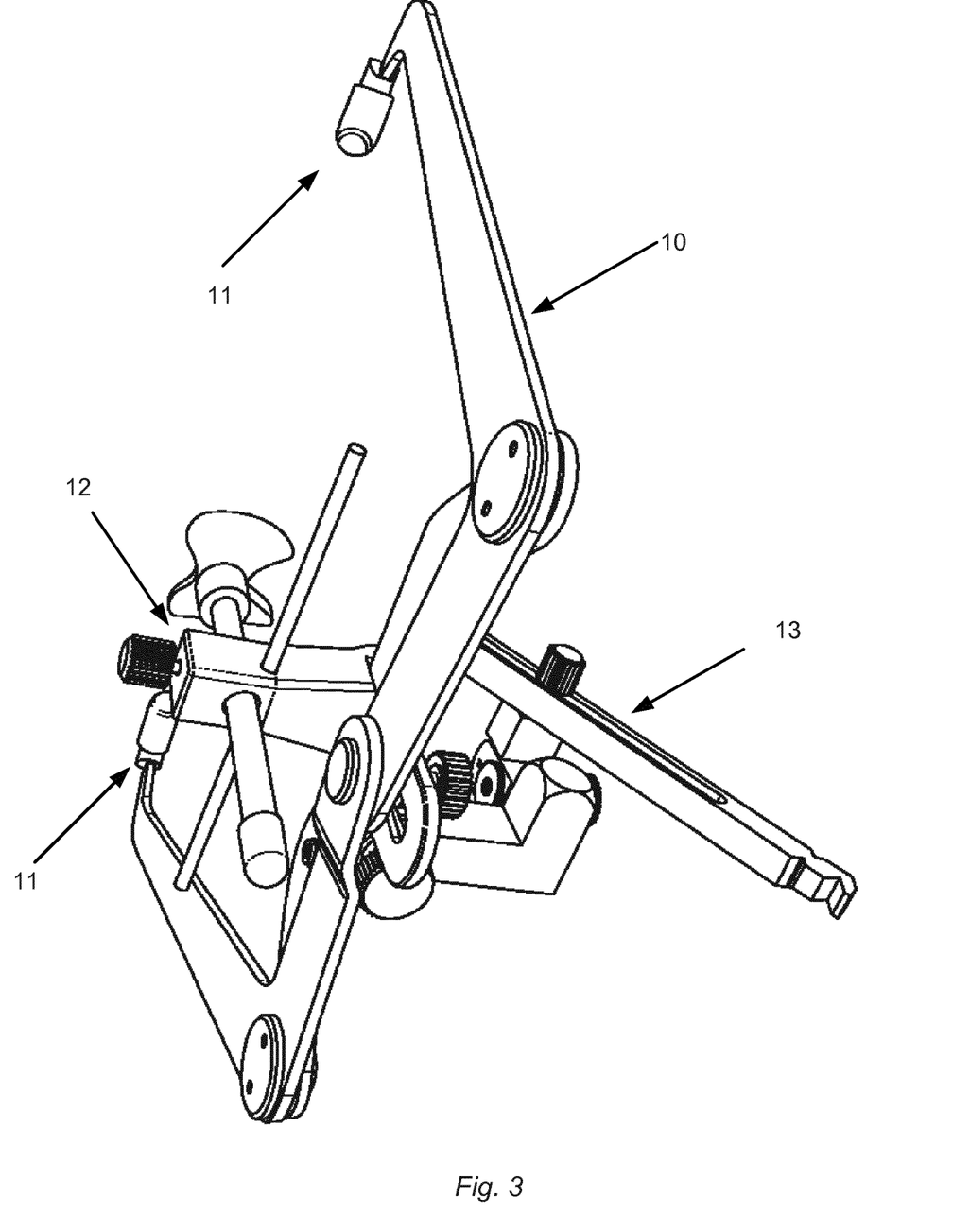
FIG. 3 shows a front view of a facebow according to an embodiment of the invention.

FIG. 3 shows a front view of a facebow according to an embodiment of the invention. The facebow comprises a U-shaped frame (10), an attachment section including ear-pieces (11), a locking device (12) for securing the facebow to the ridge of the patient's nose, and an adjustable pin member (13). When the facebow is attached to the patient, the two ear-pieces (11) will define two reference features, in this case the ear-canals, on the head of the patient. Along with the third reference point, in this case the nasion, the three reference points define a plane, which corresponds to the plane used to place the representations of the patient's jaws in a virtual and/or physical articulator. The locking device (12) is configured to securely lock the device in place, so that there is no movement of the facebow in relation to the face of the patient once the facebow has been properly attached. The adjustable pin member (13) is configured to touch the patient's dental structure when the facebow is attached to the head of the patient. It is adjustable both in a horizontal and vertical direction, so that it can be made to fit the exact geometry of the patient's face and dental structure.

Figure 4:
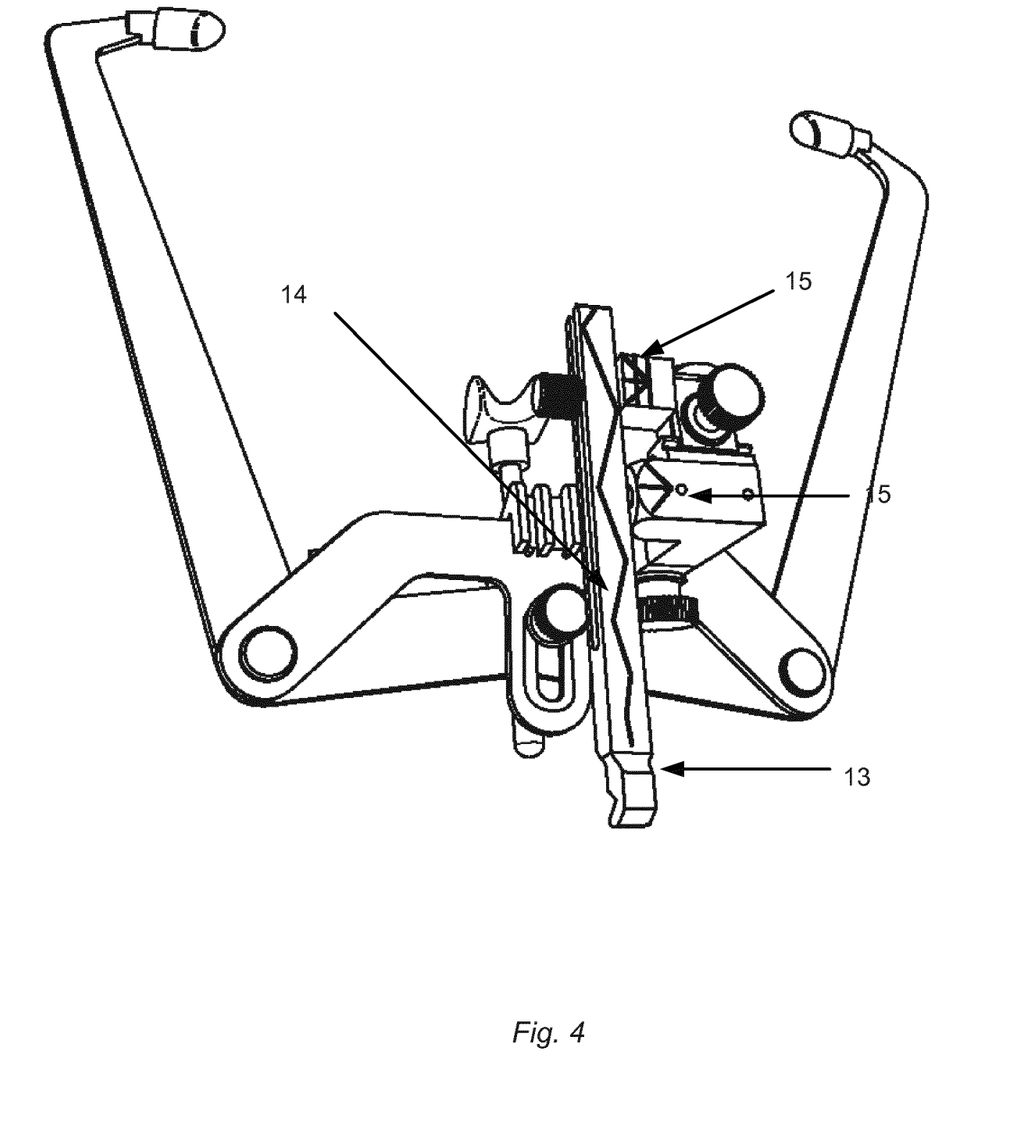
FIG. 4 shows a bottom view of a facebow according to an embodiment of the invention.

FIG. 4 shows a bottom view of a facebow according to an embodiment of the invention. The bottom view shows the underside of the adjustable pin member (13) with markings in the form of a geometric pattern (14) which is useful for stitching together the subscans of the pin member. The geometric pattern can be in any form, for example geometric shapes such as circles, squares, triangle, lines or any other shape or a random or pseudo-random pattern, or they could be colour markings. The markings could for example be etched into the pin so as to have a 3D effect when scanned, and this would make it easier to distinguish the markings in the digital representation.

Also shown is the fiducial marker (15) on the facebow, which is used to determine when enough of the facebow has been scanned, and is used to determine the geometrical relationship between the facebow and the reference feature on the patient. The facebow can have more than one fiducial marker. The fiducial marker can be anything that can easily be identified by the scanner software, for example a geometric pattern or an indentation in the form of a semi-sphere, which would make the matching of the scan of the fiducial marker with the library version of the facebow very accurate. The facebow is constructed so that the geometrical relationship between the fiducial marker and the attachment section is always approximately the same. Of course, the ear pieces can move slightly in a horizontal direction to account for the difference in diameter of the heads of different patients, but the projected distance in the vertical plane should be the same.

Figure 5:
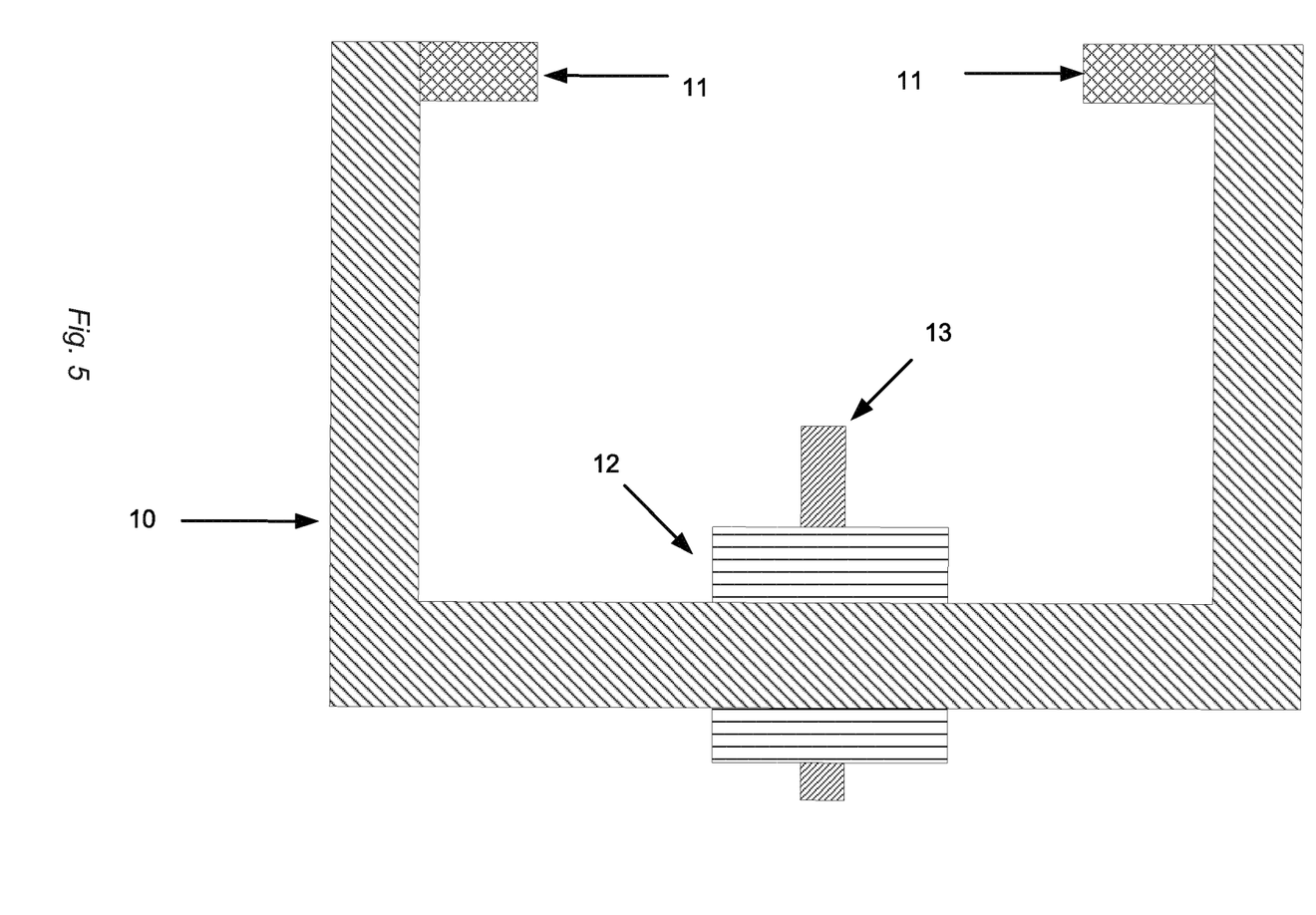
FIG. 5 shows a stylized view of a facebow according to an embodiment of the invention.

FIG. 5 shows a stylized view of a facebow according to an embodiment of the invention. The facebow has a U-shaped frame (10), an attachment section comprising condylar rods or ear pieces (11), a locking device (12) and a pin member (13) configured to touch the patient's dental structure.

Figure 6:
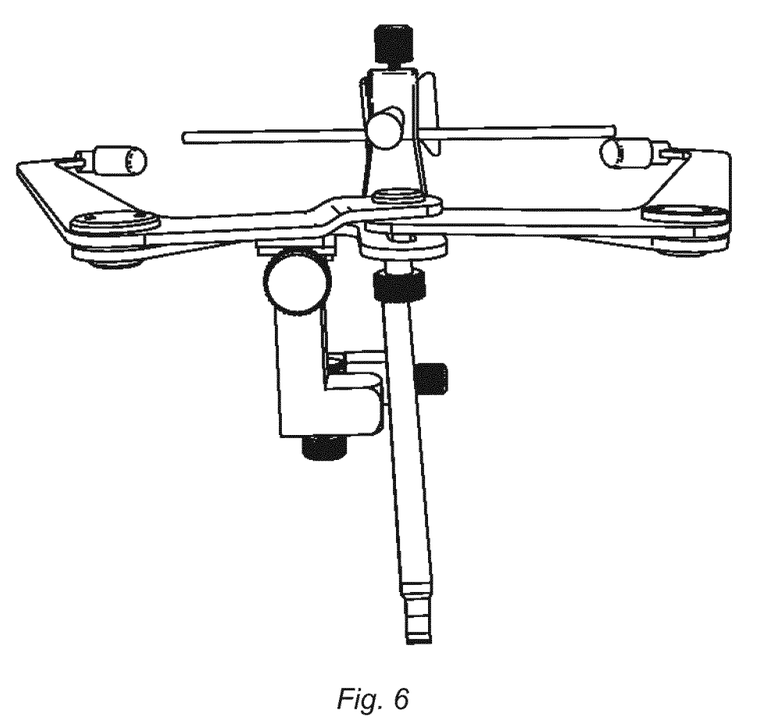
FIG. 6 shows a view of the front of the facebow.
Figure 7:
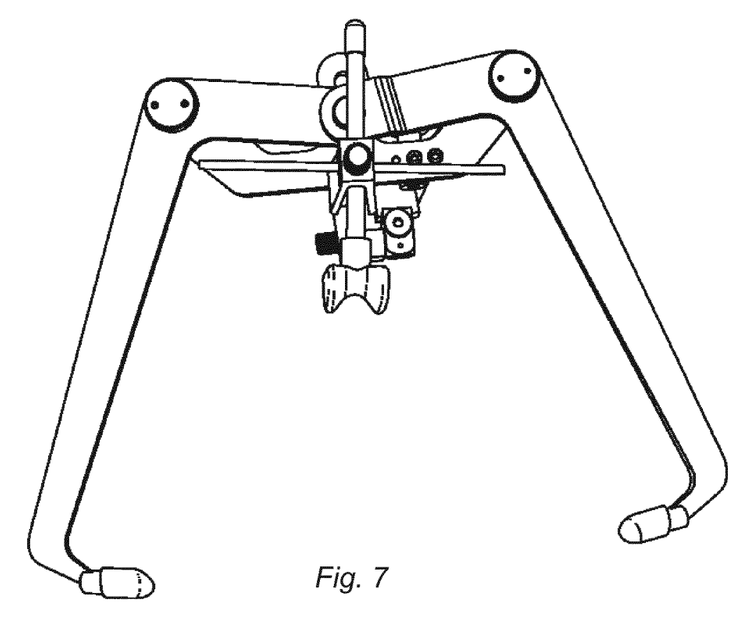
FIG. 7 shows a view of the top of the facebow.

FIGS. 6 and 7 show front and top views of the facebow respectively.

Although some embodiments have been described and shown in detail, the invention is not restricted to them, but may also be embodied in other ways within the scope of the subject matter defined in the following claims. In particular, it is to be understood that other embodiments may be utilised and structural and functional modifications may be made without departing from the scope of the present invention.

In device claims enumerating several means, several of these means can be embodied by one and the same item of hardware. The mere fact that certain measures are recited in mutually different dependent claims or described in different embodiments does not indicate that a combination of these measures cannot be used to advantage.

A claim may refer to any of the preceding claims, and "any" is understood to mean "any one or more" of the preceding claims.

It should be emphasized that the term "comprises/comprising" when used in this specification is taken to specify the presence of stated features, integers, steps or components but does not preclude the presence or addition of one or more other features, integers, steps, components or groups thereof.

The features of the method described above and in the following may be implemented in software and carried out on a data processing system or other processing means caused by the execution of computer-executable instructions. The instructions may be program code means loaded in a memory, such as a RAM, from a storage medium or from another computer via a computer network. Alternatively, the described features may be implemented by hard-wired circuitry instead of software or in combination with software.

The invention claimed is:

1. A method for determining a geometrical relationship between at least a first part of a patient's dental structure and at least one reference feature on a head of the patient in order to transfer a digital representation of the patient's dental structure into a virtual articulator, the method comprising:
   obtaining a first digital representation of a facebow including a fiducial marker, an adjustable pin member attached to the facebow and an attachment section of the facebow for placing the facebow in relation to the reference feature, the attachment section having a geometrical relationship with the fiducial marker;
   obtaining a second digital representation comprising a part of the patient's dental structure, at least a part of the pin member, and at least a part of the facebow including the fiducial marker;
   obtaining information about placement of the attachment section relative to the reference feature;
   aligning the first digital representation of the facebow with the second digital representation of the patient's dental structure; and
   determining the geometrical relationship between the part of the patient's dental structure and the reference feature based on the aligned first and second digital representations and the information about the placement of the attachment section.

2. The method according to claim 1 wherein the information about the placement of the attachment section, comprises information about which specific reference feature, on the head of the patient, the facebow was attached to.

3. The method according to claim 1, wherein determining the geometrical relationship between the patient's dental structure and the reference feature comprises:
   defining a co-ordinate system;
   inserting and aligning the first and second digital representations in the co-ordinate system so that common features overlap;
   calculating the geometrical relationship between the patient's dental structure and the reference feature based on the known relationship between the overlapping features and the reference feature.

4. The method according to claim 1, the method further comprising:
   obtaining a third digital representation comprising the patient's upper jaw;
   aligning the second and third digital representations in a common co-ordinate system; and
   coupling the information about the geometrical relationship to the third digital representation.

5. The method according to claim 4, further comprising:
   obtaining a fourth digital representation comprising the lower jaw of the patient;
   obtaining a fifth digital representation comprising at least part of the upper and lower jaws in occlusion.

6. The method according to claim 1, further comprising:
   transferring one or more of third, fourth or fifth digital representations into a virtual articulator based on the geometrical relationship between the patient's dental structure and the at least one reference feature.

7. The method according to claim 1, wherein obtaining the digital representations comprises scanning using an intraoral scanner.

8. The method according to claim 1, wherein the reference feature comprises one or more of the ear canal, the temporomandibular joint, the nasion, the ala of the nose, and/or the orbitale, and wherein the reference feature(s) is used to determine one of the Frankfort plane, the Camper plane, the Denar plane, the maxilla plane, the mandible plane and/or the occlusal plane, and this plane is used in transferring the digital representation into the virtual articulator.

9. The method according to claim 1, wherein the first digital representation of the facebow with the second digital representation of the patient's dental structure are aligned in a co-ordinate system.

10. The method according to claim 1, wherein the aligning of the first digital representation of the facebow with the second digital representation of the patient's dental structure is based in part on aligning the fiducial marker that is in the first digital representation and in the second digital representation.

11. A method of transferring a digital representation of a patient's dental structure into a virtual articulator, whereby the geometrical relationship between at least a first part of a patient's dental structure and at least one reference feature on the head of the patient is determined, the method comprising:
   obtaining a first digital representation of a facebow including a fiducial marker, an adjustable pin member attached to the facebow, and an attachment section of the facebow for placing the facebow in relation to the reference feature, the attachment section having a geometrical relationship with the fiducial marker;
   obtaining a second digital representation comprising a part of the patient's dental structure, at least a part of the pin member, and at least a part of the facebow including the fiducial marker;
   obtaining information about the placement of the attachment section relative to the reference feature, whereby the information about the placement of the attachment section comprises information about which specific reference feature on the head of the patient the facebow was attached to;
   determining the geometrical relationship between the part of the patient's dental structure and the reference feature based on the first and second digital representations and the information about the placement of the attachment section;
   obtaining a third digital representation comprising the patient's upper jaw;

aligning the second and third digital representations in a common coordinate system;

coupling the information about the geometrical relationship to the third digital representation;

obtaining a fourth digital representation comprising the lower jaw of the patient;

obtaining a fifth digital representation comprising at least part of the upper and lower jaws in occlusion; and transferring one or more of the third, fourth or fifth digital representations into the virtual articulator based on the geometrical relationship between the patient's dental structure and the at least one reference feature.

12. The method according to claim 11, wherein determining the geometrical relationship between the patient's dental structure and the reference feature comprises:

defining a co-ordinate system;

inserting and aligning the first and second digital representations in the co-ordinate system so that common features overlap;

calculating the geometrical relationship between the patient's dental structure and the reference feature based on the known relationship between the overlapping features and the reference feature.

13. The method according to claim 11, further comprising:

aligning the first digital representation of the facebow with the second digital representation of the patient's dental structure in a co-ordinate system; and determining the geometrical relationship between the part of the patient's dental structure and the reference feature is done based on the aligned first and second digital representations and the information about the placement of the attachment section.

\* \* \* \* \*